(12) United States Patent
Moroni

(10) Patent No.: US 7,083,644 B1
(45) Date of Patent: Aug. 1, 2006

(54) IMPLANTABLE PROSTHESES WITH IMPROVED MECHANICAL AND CHEMICAL PROPERTIES

(75) Inventor: Antonio Moroni, Morris Plains, NJ (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/577,790

(22) Filed: May 24, 2000

(51) Int. Cl.
*A61F 2/06* (2006.01)

(52) U.S. Cl. .................................. 623/1.51; 623/23.71

(58) Field of Classification Search ............... 623/1.49, 623/1.54, 11.11, 23.64, 23.71, 2.36, 2.39, 623/2.4, 2.41, 1.13, 1.5, 1.51, 1.53; 139/383 R, 139/387 R, 420; 428/36.1; 442/5
See application file for complete search history.

(56) References Cited

U.S. PATENT DOCUMENTS

| | | | |
|---|---|---|---|
| 4,001,479 A | | 1/1977 | Hamana et al. |
| 4,026,973 A | | 5/1977 | Shima et al. |
| 4,331,697 A | * | 5/1982 | Kudo et al. ..................... 427/2 |
| 4,996,269 A | | 2/1991 | Richeson et al. |
| 5,217,495 A | | 6/1993 | Kaplan et al. ............. 623/13.18 |
| 5,292,802 A | * | 3/1994 | Rhee et al. .................. 424/422 |
| 5,422,068 A | * | 6/1995 | Shalaby et al. ................ 422/22 |
| 5,443,499 A | | 8/1995 | Schmitt |
| 5,466,525 A | | 11/1995 | Maria et al. |
| 5,562,725 A | | 10/1996 | Schmitt et al. |
| 5,628,957 A | | 5/1997 | Collette et al. |
| 5,681,322 A | | 10/1997 | Hartigan, Jr. |
| 5,697,970 A | | 12/1997 | Schmitt et al. |
| 5,800,514 A | | 9/1998 | Nunez et al. |
| 5,871,468 A | * | 2/1999 | Kramer et al. ........... 604/96.01 |
| 5,876,436 A | * | 3/1999 | Vanney et al. .............. 623/2.39 |
| 5,980,564 A | * | 11/1999 | Stinson ..................... 623/23.7 |
| 6,346,119 B1 | * | 2/2002 | Kuwahara et al. ......... 623/1.13 |

FOREIGN PATENT DOCUMENTS

| | | | |
|---|---|---|---|
| EP | 461791 | * | 3/1991 |
| EP | 0 855 170 A2 | | 7/1998 |
| WO | WO 9904727 A1 | * | 2/1999 |
| WO | WO 99/12585 | | 3/1999 |

* cited by examiner

*Primary Examiner*—Brian E Pellgrino
(74) *Attorney, Agent, or Firm*—Hoffmann & Baron, LLP

(57) ABSTRACT

Prostheses with improved chemical and mechanical properties manufactured that includes a radiation resistant and hydrolytically stable biocompatible fabric having outer and first and second ends with a textile fabric that includes a naphthalene dicarboxylate derivative polymer having the general formula:

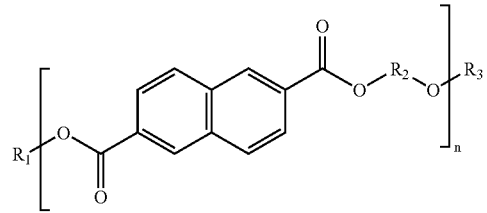

wherein $R_1$ and $R_3$ are the same or different groups and are independently selected from the naphthalene dicarboxylate derivative repeating unit (I), a hydrogen radical and a methyl radical. $R_2$ is an alkylene radical having 1 to 6 carbon atoms; n is from 10 to 200. Also contemplated are implantable prostheses that are flat constructions useful as patches and filters or tubular constructions useful as vascular grafts. A further aspect of this invention provides a method for making a radiation and thermal resistant and hydrolytically stable, steam sterilizable biocompatible prosthesis.

17 Claims, 6 Drawing Sheets

IMPLANTABLE PROSTHESES WITH IMPROVED MECHANICAL AND CHEMICAL PROPERTIES

FIELD OF THE INVENTION

The present invention relates to an implantable textile prosthesis. More, specifically, the present invention relates to an implantable textile prosthesis having substantially improved chemical and mechanical properties by the incorporation of yarns made from a naphthalene dicarboxylate (NDC) derivative.

BACKGROUND OF RELATED TECHNOLOGY

Conventional textile implantable prostheses are manufactured using yarns made of biocompatible and biostable material. One polymeric material widely used in conventional implants is polyethylene terephthalate (PET.) This material has been found to be especially useful in vascular grafts and stent grafts, as well as other textile implants such as patches, surgical mesh, sutures, filters, ligaments and the like. Further applications of PET include surgically implanted vascular grafts and endoluminal vascular grafts implanted by minimally invasive procedures.

Prostheses desirably exhibit long term wear and kink resistance so that they do not have to replaced as often. Many current designs include a metal stent attached to an endoluminal graft to form a composite device for implantation. Typically, the fabrics used in these types of textile constructions are subjected t to strenuous conditions such as constant rubbing against the stent during pulsation of blood. Such abrasive forces can result in weakening of current PET textile grafts which can result in loss of structural integrity and in extreme cases graft failure. Additionally, in applications involving peripheral vessels, current textile fabrics, such as those made from PET, are less kink resistant than desired. This may especially be a problem for prostheses used in smaller passageways such as those found in legs or children. Thus, there is a need for more durable fabrics that are capable of being incorporated into vascular prostheses for use in peripheral vessels.

Prostheses are desirably implanted into the body without introducing sources of infection in the body. Thus, in addition to being strong and durable, textile materials used for implantable devices must also be able to undergo sterilization procedures. To minimize infectious sources introduced by the implantation of prostheses, sterilization methods, such as gas sterilization, have been utilized. Unfortunately, gas sterilization methods do not guarantee that virulent strains of bacteria and viruses will be killed. The emergence of antibiotic resistant strains of bacteria have made sterilization an even more important issue. Traditional prostheses, such as those manufactured with PET fabrics, cannot tolerate more powerful methods of sterilization, such as radiation or steam sterilization, without risking degradation of the fabric. These degradative effects might seem to be minimal at first, but over the lifetime of its implant can prove to be significant enough to compromise the structural integrity and stability of the textile in vivo. Thus, it would be desirable to be able to manufacture prostheses that can be treated with more powerful sterilization methods, such as steam sterilization, prior to implantation to eliminate possible sources of infection from the prosthesis. Steam sterilization is also desirable in emergency situations when quick implantation of the graft is necessary or more sophisticated methods are not available.

Accordingly, it is desirable to provide an implantable textile prostheses with improved chemical and mechanical properties so that the prostheses will overcome the deficiencies of the currently available textile prostheses. In particular, it would be desirable to develop a new implantable textile prosthesis having higher modulus and tensile strength, enhanced abrasion resistance, higher thermal and radiation resistance, self-sealing properties and greater hydrolytic stability.

SUMMARY OF THE INVENTION

The present invention seeks to solve the deficiencies of the currently available prostheses. More specifically, the present invention provides prostheses with improved chemical and mechanical properties manufactured with a textile fabric that includes a naphthalene dicarboxylate derivative polymer having the general formula:

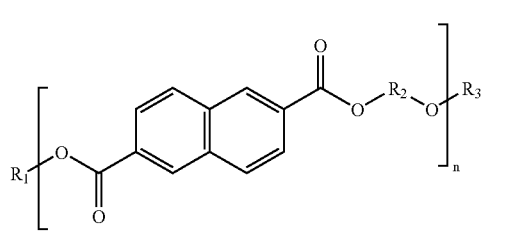

wherein $R_1$ and $R_3$ are the same or different groups and are independently selected from the group consisting of hydrogen and methyl radicals. $R_2$ is an alkylene radical having 1 to 6 carbon atoms which may be the same or different and may be linear or branched; and n is from 10 to 200.

In one aspect of the invention, the present invention includes an implantable prosthesis having improved mechanical and chemical properties including a radiation resistant and hydrolytically stable biocompatible fabric having a textile construction of a plurality of polymeric filaments comprising a naphthalene dicarboxylate derivative. These filaments are generally bundled into yarns which can then be woven, braided or knitted or otherwise combined into a textile fabric. Such fabrics can be flat constructions, which can be used as is for such applications as patches or filters. Alternatively, flat woven tubular conduits can be fashioned, such as those used as vascular grafts.

Another aspect of this invention includes an implantable prosthesis having improved mechanical and chemical properties including a radiation resistant and hydrolytically stable biocompatible tubular fabric of a textile construction, said fabric having a plurality of yarns selected from the group consisting of polyethylene naphthalate, polybutylene naphthalate, polytrimethylene naphthalate, trimethylenediol naphthalate, and combinations thereof.

NDC yarns can be spun into prostheses having excellent performance profiles including improved mechanical and thermal properties such as excellent resistance to degradation by oxygen, UV light, moisture and other chemicals, particularly at elevated temperatures.

NDC yarns have increased resistance to hydrolysis at elevated cylinder temperatures, a good dry heat resistance, at least comparable tensile strength and modulus to PET, with maintenance of properties at the higher operating temperatures, good mechanical properties under dynamic operating conditions, to include abrasion resistance and loop strength, and the ability to maintain crimp at the operating temperatures involved with the concomitant resistance to long term fabric creep.

Naphthalene carboxylate derivatives yarns show improved resistance to radiation, heat and steam. Accordingly, a further aspect of this invention provides a method for making a radiation and thermal resistant and hydrolytically stable, steam sterilizable biocompatible prosthesis including the steps of providing a fabric having an inner and outer surface and first and second ends, said fabric having a plurality of polymeric filaments comprising a dicarboxylate naphthalene derivative; selecting a textile construction pattern; and forming said prosthesis in accordance with a textile construction pattern.

DETAILED DESCRIPTION OF THE INVENTION

Figure 1:
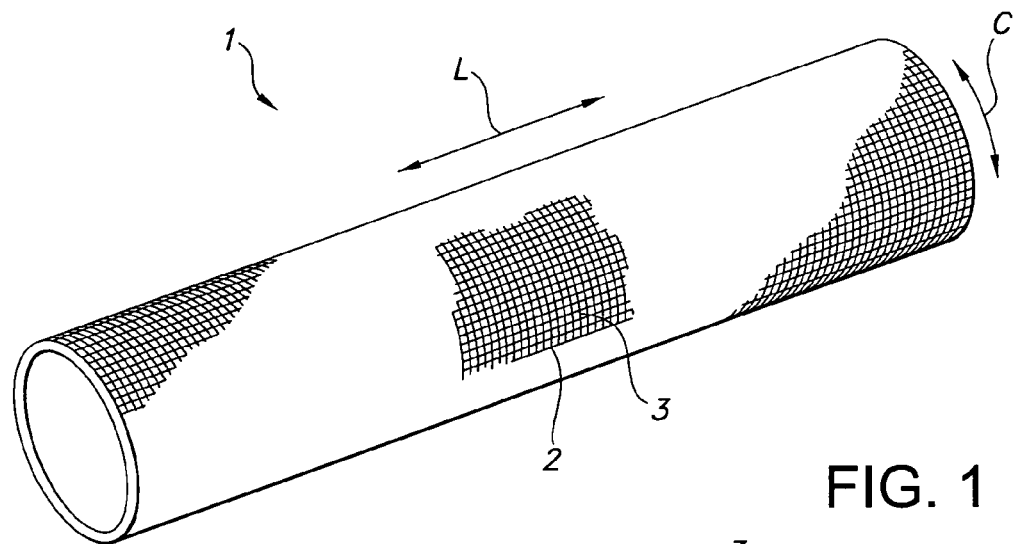
FIG. 1 is a perspective view of a tubular woven tubular prosthesis useful in the present invention.

The present invention seeks to solve the deficiencies of the prior art by making prostheses having improved chemical and mechanical properties with a textile fabric made from a naphthalene dicarboxylate derivative polymer having the general formula:

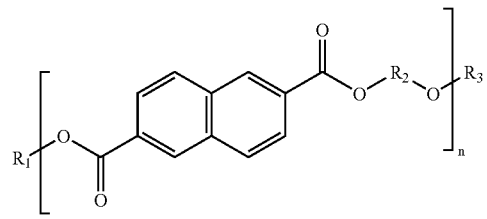

wherein $R_1$ and $R_3$ are the same or different groups and are independently selected from the group consisting of hydrogen radicals and methyl radicals. $R_2$ is an alkylene radical having 1 to 6 carbon atoms which may be the same or different and may be linear or branched; and n is from about 10 to 200. Preferably, $R_2$ is linear. Intrinsic viscosity is from about 0.15 to about 1.80 dl/g, desirably from about 0.50 to about 0.79 dl.g.

More particularly, the present invention includes an implantable prosthesis manufactured with a radiation resistant and hydrolytically stable biocompatible fabric having a textile construction of a plurality of polymeric filaments. At least a portion of these polymeric filaments are composed of a naphthalene dicarboxylate derivative. Any naphthalene dicarboxylate derivative which provides improved chemical and/or mechanical properties as compared to conventional textiles such as PET may be used, including poly(ethylene naphthalate), poly(propylene naphthalate), polytrimethylene naphthalate, trimethylenediol naphthalate, poly(iso-propylene naphthalate), poly(n-butylene naphthalate), poly(iso-butylene naphthalate), poly(tert-butylene naphthalate), poly(n-pentylene naphthatate), poly(n-hexylene naphthalate), and combinations and derivatives thereof. Useful naphthalene dicarboxylate acid isomers for PEN polymers include 1,2-, 1,3-, 1,4-, 1,5-, 1,6-, 1,7-, 1,8-, 2,3-, 2,4-, 2,5-, 2,7-, and 2,8-isomers. Diesters of 2,6-naphthalene dicarboxylic acid are the preferred esters for use in this invention. Among the specific naphthalene dicarboxylate polymers found to be particularly desirably for prostheses of the present invention is poly(ethylene 2,6 naphthalene dicarboxylate).

An advantage of PEN is that its Tg is higher than PET so that it can be processed under stronger conditions than PET without losing its shape or dimension. Thus, PEN should not only be able to successfully undergo heat treatment and radiation sterilization but its higher chemical and hydrolytic stability should allow a PEN prosthesis to undergo steam sterilization without dimensional instability or undue degradation. Steam sterilization has certain advantages over other types of sterilization techniques including the fact that it may be used in emergency cases when quick implantation of the prosthesis is necessary or more sophisticated methods are not available.

PEN fibers have lower heat shrinkage, a property that could be used to produce more dimensionally stable prostheses. The high tenacity and modulus of PEN yarns and filaments are maintained even at high temperatures and PEN fibers show excellent resistance to abrasion and looping. Table I and II compare the properties of PEN and other yarns. These properties could allow PEN to be spun into thinner fibers and finer yarns which may allow the manufacturing of thinner grafts, an especially useful quality for grafts that are loaded into thin endoprosthetic devices. Additionally, the prostheses of the present invention can be made thinner and/or stronger without affecting its effectiveness, which is a significant advantage when a prosthesis is to be loaded into a catheter and delivered intraluminally via a catheter.

Yarns made with PEN have a high tenacity which can be applied to realize high puncture resistant A-V access grafts. Furthermore, the higher modulus of PEN yarns, which is about twice that of PET, may be employed to provide a prosthesis with a greater resistance to kinking. These properties of the polymeric fibers increase the durability of prostheses, thereby reducing the need for physicians to routinely remove, repair and replace vascular prostheses that have been implanted.

Figure 6:
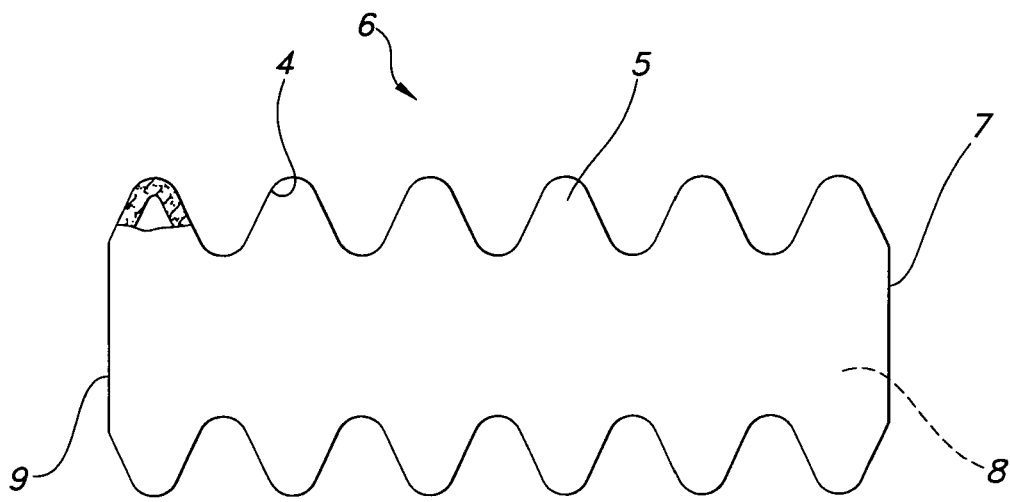
FIG. 6 shows schematically, in partial section, a prosthesis of the present invention with a series of wave-like crimps.

Once deployed, the inventive prosthesis desirably maintains its longitudinal flexibility and returns to its tubular open lumen configuration so that the lumen remains open allowing the passage of blood. As shown in FIG. 6, crimps 4 may optionally be employed with the present invention to permit such longitudinal flexibility and structural integrity without increasing the graft thickness as measured by both fabric wall thickness and as measured between the peak-to-peak amplitude of the wave-like pattern of crimps. The prosthesis 6 includes a generally tubular body 5 having opposing ends 7 and 9 which define therebetween an open lumen 8 which permits passage of blood once the graft 6 is implanted in the blood vessel.

The prosthesis may include a radiopaque guideline or marker to provide means for viewing the implanted prosthesis fluoroscopically. The marker may extend the length of the prosthesis. Other patterns for markers may also be employed. Radiopaque markers assist the surgeon to visualize the prosthesis both during and after implantation. The marker helps show the surgeon that the prosthesis is properly positioned. Also, it will indicate whether the prosthesis has dilated or collapsed after implantation.

As is well known, radiopaque guidelines or markers may be formed from metallic fibers such as stainless steel or titanium. Also, one or more of the fibers made from a naphthalene dicarboxylate derivative may be coated or filled with radiopaque particles.

Virtually any type of implantable prosthesis can be made from the present invention due to the versatility of the naphthalene dicarboxylate fibers. Particularly desirable applications include intraluminal prostheses, such as endovascular grafts, blood filters, stent-graft composites and the like. This invention may also be designed to repair or support a weakened or damaged lumen, such as a blood vessel in the vascular system. Alternatively, the present invention may be utilized as a balloon catheter, mesh, vascular patch, hernia plug and the like.

Figure 11:
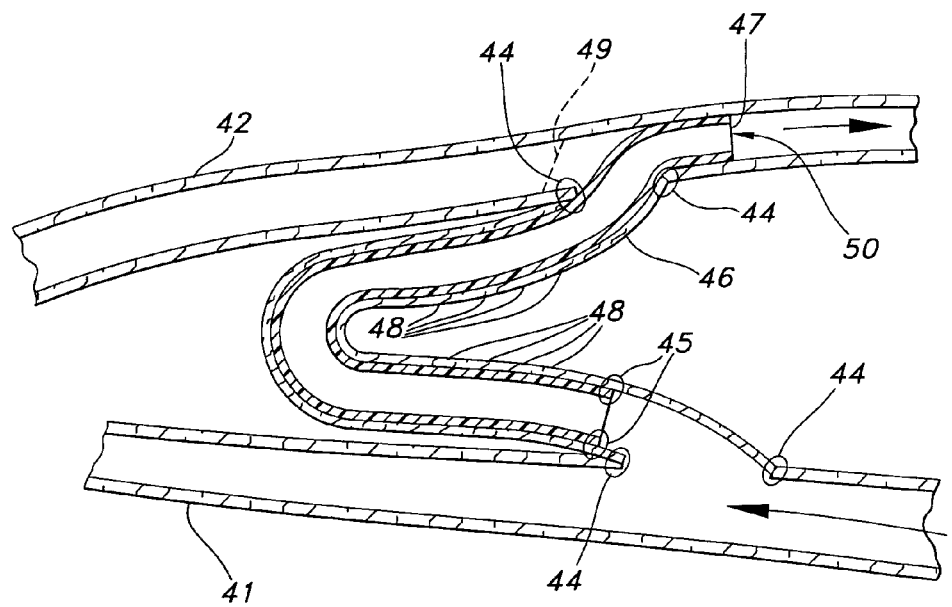
FIG. 11 describes a cross section of an arteriovenous vascular graft.

This invention also contemplates an arterial-venous (AV) access graft as shown in FIG. 11. Naphthalene dicarboxylate derivative polymers with high tenacity are capable of producing AV access grafts which exhibit self-sealing features. Consequently, the self-sealing AV access grafts of this invention do not need coating additives or application of external pressure to seal as may be required by conventional AV access grafts.

FIG. 11 depicts a cross section showing optional interior liner 50 used to repair vascular graft 46. Graft 46 is anastomosed to artery 41 and vein 42 by sutures 44. The arterial end of the liner 50 is secured to the arteriovenous graft 46 by sutures 45. The venous end 47 of the liner 50 may be left without direct mechanical attachment such as by sutures. Vein 42 may be ligated if desired at site 49 adjacent to the anastomosis of the vein 42 and arteriovenous graft 46. Liner 50 covers old cannulation sites 48.

Another aspect of the invention contemplates an implantable prosthesis that is composed of a tubular fabric. Examples of prostheses that may require a tubular design include intraluminal prostheses, endovascular grafts, radially deformable support components, such as radially deformable stents.

More specifically, use of this invention with self-expanding stents and balloon expandable stents are also contemplated. Self-expanding stents include those that have a spring-like action which causes the stent to radially distend (expand and contract) or stents which expand due to the memory properties of the stent material for a particular configuration at a certain temperature. Fabrics made from a naphthalate dicarboxylate derivative will perform well in conjunction with stents due to the durability and abrasion resistance of the fabric. As mentioned above, stent-graft composite devices often pulsate in the body in accordance with the passage of blood. Such movement may cause abrasion of the graft by the metal stent, leading to a weakening of the integrity of the prosthesis.

Figure 2:
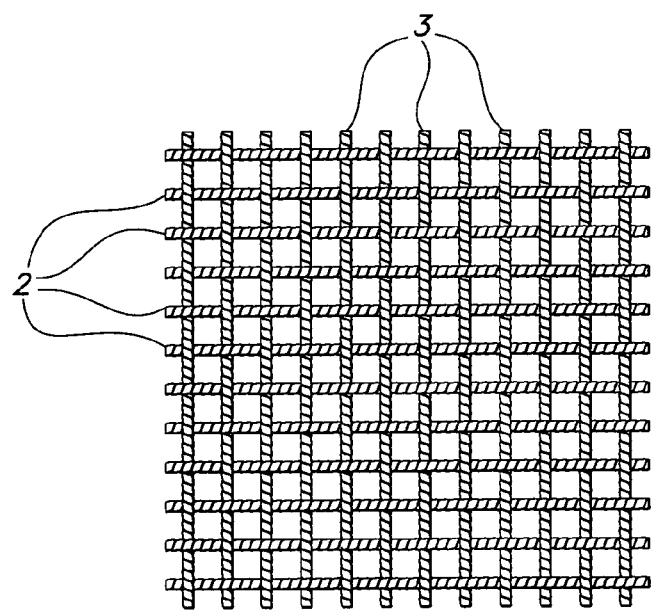
FIG. 2 is a schematic of a conventional weave pattern useful in the present invention.
Figure 3:
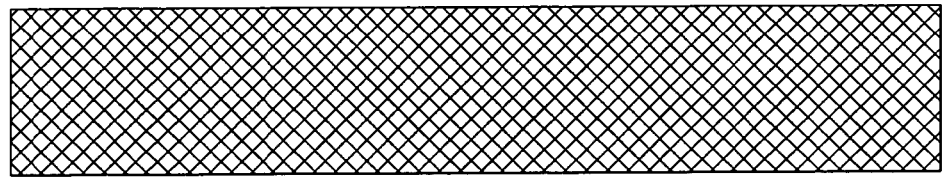
FIG. 3 is a perspective view of a braided tubular prosthesis useful in the present invention.
Figure 3A:
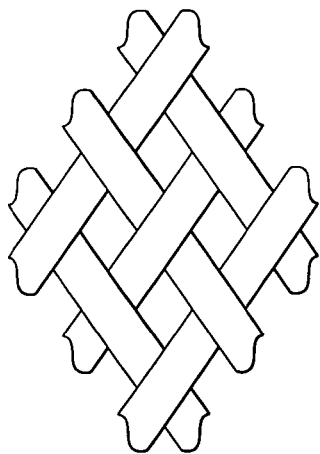
FIG. 3A is a schematic of a diamond braid useful in the present invention.
Figure 3B:
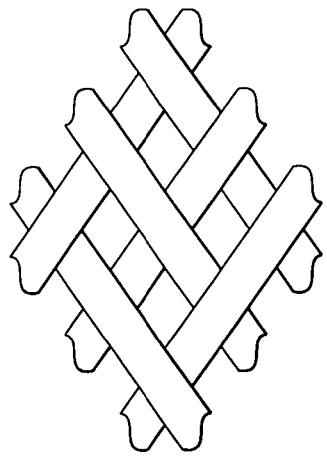
FIG. 3B is a schematic of a regular braid useful in the present invention.
Figure 3C:
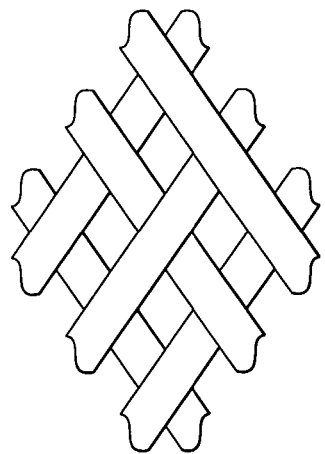
FIG. 3C is a schematic of a hercules braid useful in the present invention.

Fabrics made from the filaments can have virtually any textile construction, including weaves, knits, braids, filament windings and the like. Fabrics made from spun filaments are also contemplated. Referring to the drawings and, in particular to FIGS. 1–2, a woven tubular prosthesis is shown. The weave pattern includes warp yarns 2 running along the longitudinal length (L) of the woven product and fill yarns 3 running around the circumference (C) of the product the warp, the fill yarns being at approximately 90 degrees to one another with fabric flowing from the machine in the warp direction. The yarns used in a woven product may be treated and processed prior to weaving. This treatment commonly includes the step of "drawing" the yarns, that is, longitudinally stretching the yarns beyond their point until complete plastic deformation (i.e., a region in which the yarn now exhibits loss of its elasticity and ability to change appreciably in length) is accomplished.

A prosthesis that is woven with undrawn or a combination of undrawn and partially drawn radial yarns is also contemplated. Such prostheses will be capable of circumferential expansion following manufacture of the product. For instance, if a balloon catheter (or similar device) is inserted into such a prosthesis and is thereafter expanded, the prosthesis will circumferentially expand a slight degree until the yield point is reached. At that point, the radial yarns, i.e. fill yarns, which were not drawn, will plastically deform, thereby allowing substantial circumferential expansion.

The force required to "draw" a yarn increases until the yield point is reached, at which point, the yarn enters a region of plastic deformation. Once the deformation point in a yarn has been reached through stretching, the material has substantially lost its elastic memory and is more or less "fixed", neither being able to be further stretched or to return to its original length. Polyethylene naphthalate yarns are capable of full deformation through the drawing process to make prostheses that desirably maintain constant pressures without concern for undesirable stretching or bulging during use. Thus, these prostheses retain their expanded circumferential length and now have a fixed diameter.

The yarn may also be stretched until a point at which the material fractures, i.e., the fracture point. The process of drawing the yarn to a point prior to the fracture point, increases the tensile strength of the yarn and decreases the elongation to failure. As a result of drawing, the polymeric yarns become directionally aligned or oriented. An advantage of PEN is that it can be processed under stronger conditions than PET without losing its shape or dimensions.

Figure 9:
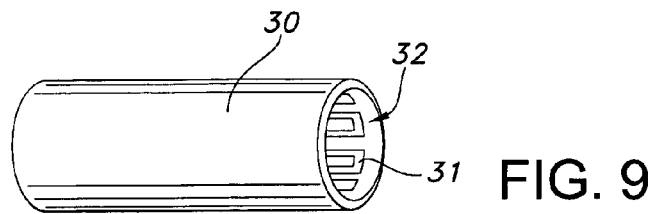
FIG. 9 is a perspective showing of a prosthesis and a stent-graft composite of the present invention with a stent incorporated therein.
Figure 10:
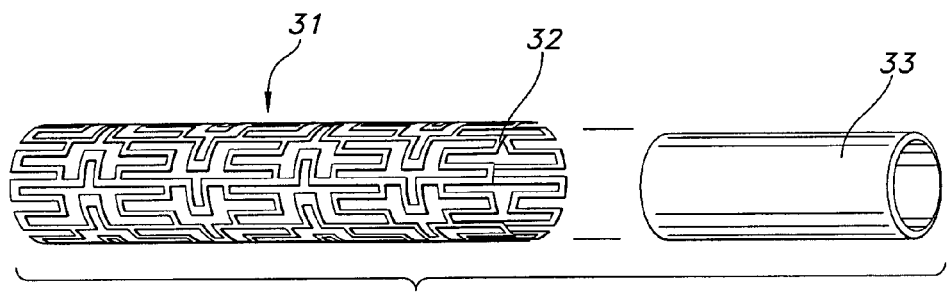
FIG. 10 is a perspective showing a stent with an inner graft liner.

To secure the prosthesis to the host lumen, a stent may be incorporated in the prosthesis as shown in FIGS. 9 and 10. In that way, both the prosthesis 30 and the stent 31 can be simultaneously and controllably expanded to the desired diameter or until the stent/graft composite 32 substantially conforms to the diameter of the host lumen. Any suitable means of attaching the stent 31 to the expandable prosthesis 30, such as hooks, catches, sutures or other similar means may be used. Incorporating the stent 31 between layers of fabric or graft walls 30 and 31 to form a composite structure is also contemplated. Additionally, the stent 31 may include similar means capable of anchoring the prosthesis in place in the host lumen. This is often accomplished by expanding the stent-graft structure such that sufficient radial pressure against the luminal surface of the vessel provides for anchoring. Alternatively or in addition to anchoring using a sufficiently tight radial fit, various barbs or hooks may be used to secure the prosthesis in place in the host vessel.

The yarns used in forming the prostheses of the present invention may be flat, twisted, textured or combinations thereof, and may have high, low or moderate shrinkage properties. Additionally, the yarn type and yarn denier can be selected to meet specific properties desired for the prosthesis, such as porosity, flexibility and compliance. The yarn denier represents the linear density of the yarn. Thus, yarn of small denier, e.g., 40–50 denier, would correspond to a very fine yarn whereas a yarn with a larger denier, e.g. 1,000, would correspond to a heavy yarn.

Yarns useful in the inventive prostheses have a denier range from about 20 to about 1500 and a filament count of about 10 to about 200, depending on the specific type of vascular graft desired. The yarns used with the present invention preferably have a denier from about 20 to about 300. A high filament count for the same overall linear density increases the yarns flexibility, reduces its stiffness and reduces permeability to viscous liquids, i.e. blood. Thus, a PEN prosthesis can be made of a large number of filaments for the same overall stiffness, thus making it less permeable. A particularly useful filament count is from about 20 to about 30 with a corresponding 30 denier.

As mentioned above, a variety of textile constructions may be employed using the present invention. With respect to weaves, any known weave pattern in the art, including, simple weaves, basket weaves, twill weaves, velour weaves and the like may be used. Although weaving and knitting are among the most desirable constructions, braiding may also be used as shown, for example, in FIGS. 3 and 3A–3C. Braiding of yarns includes the interlacing of two yarn systems such that the path of the yarns are diagonal to the fabric delivery direction, forming either a flat or tubular structure. A multi-layered braided structure is defined as a structure formed by braiding wherein the structure has a plurality of distinct and discrete layers. These layers may be bound by interlocking yarns or by adhesive laminates, sewing or the like.

Figure 7:
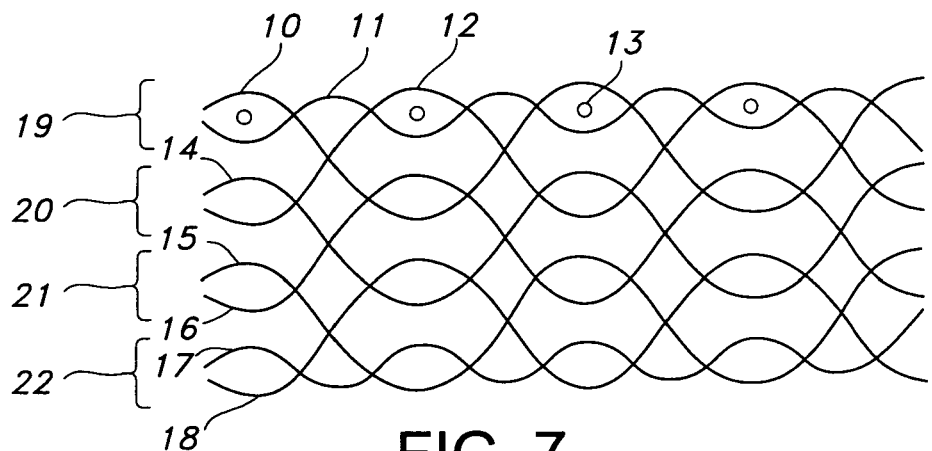
FIG. 7 is a cross-sectional view of a portion of a multi-layered interlocked three-dimensional braided prosthesis formed in accordance with an embodiment of the present invention.

An interlocking three-dimensional braid, as shown in FIG. 7, may be used and is defined as a braided structure having at least two layers, whereby a yarn is interbraided from a first layer into a contiguous second layer to interlock the layers of the multi-layer braid. Referring to FIG. 7, the prosthesis of the present invention includes four layers, 19, 20, 21 and 22, with each layer having at least one interlocking yarn from a contiguous layer. The interlocking yarns are braided into the structure so that the yarn forms part of the first layer, as well as being part of the contiguous layer by forming the interlock. Within each layer, a segment of the braid is formed by an interlocking yarn from a contiguous layer, the layers being interbraided together. The interlocking yarns couple the multiple layers together to form a three-dimensional braid.

In FIG. 7, the first layer 19 forms the outer layer of the interlocking three-dimensional braided structure. The outer layer is formed from a yarn 11 which is exclusively braided into the first layer along with a yarn 10 which is interbraided into a second layer which is contiguous with the first layer and a yarn 12 which is interbraided from the second layer up into the first layer. The second layer 20 is formed from segments of four yarns 10, 12, 14 and 16 which are interbraided.

The next contiguous layer 21 is formed from segments of four yarns 14, 15, 16 and 18 interbraided to form an inner layer in the multilayered structure. Layer 22 is formed in similar fashion, having three yarns 15, 17 and 18 which are interbraided.

Figure 8:
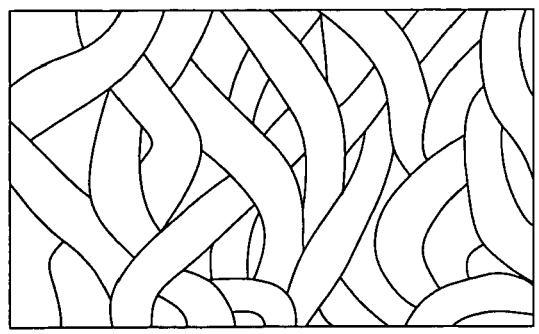
FIG. 8 is a schematic of an enlarged cross-section of a solid three-dimensional braided structure formed in accordance with one embodiment of the present invention.

A solid three-dimensional braided structure, as shown in FIG. 8, may be used and is formed by continuous intertwining of the fibers. Solid three-dimensional braids are homogenous in that all yarns are present throughout the thickness of the braid. Typically, three-dimensional braiding machines used to form this type of solid braid include an array of fiber bobbins held in ring or track configurations. Circumferential motion of the array of the bobbins to form the braid is accomplished by shifting slotted rings containing the fiber holders. Fibers are directed through the thickness of the braid by shifting the holders between the rings. Reversal of the direction of ring and hold motions during the shift segment interlocks the fibers. Since every fiber undergoes a similar motion, all fibers become entwined in the balanced array as illustrated in FIG. 8.

Figure 4:
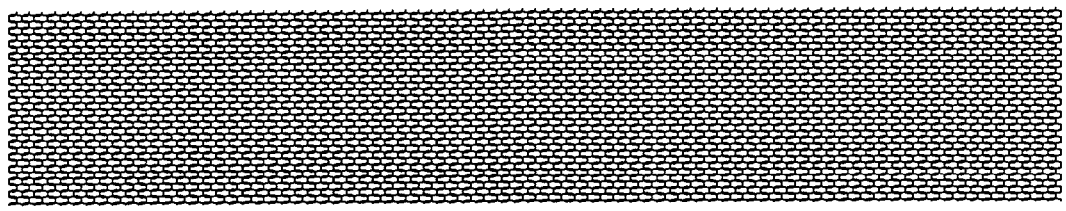
FIG. 4 is a perspective view of a knitted tubular prosthesis useful in the present invention.
Figure 4A:
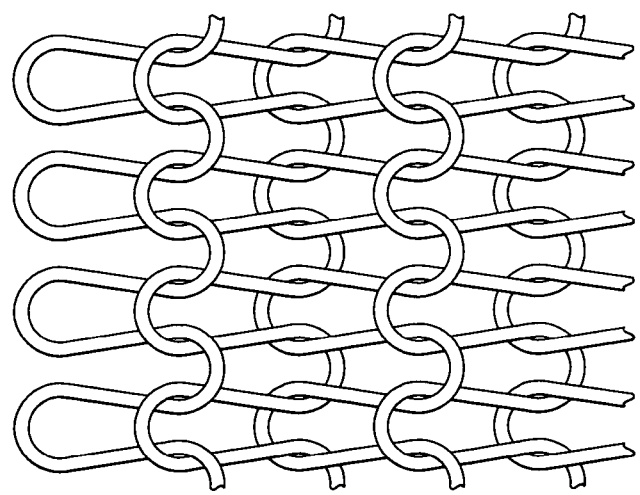
FIG. 4A is an enlarged detail of FIG. 4.
Figure 5:
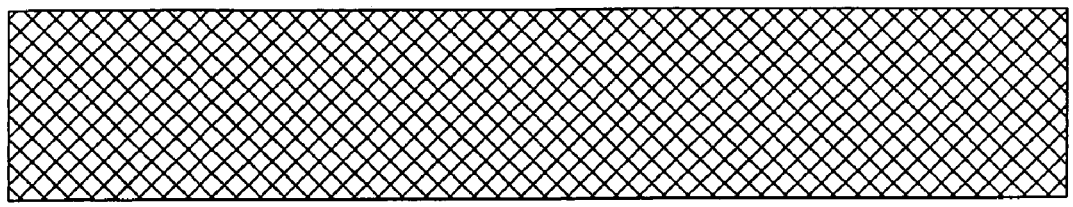
FIG. 5 is a perspective view of a filament wound tubular prosthesis useful in the present invention.
Figure 5A:
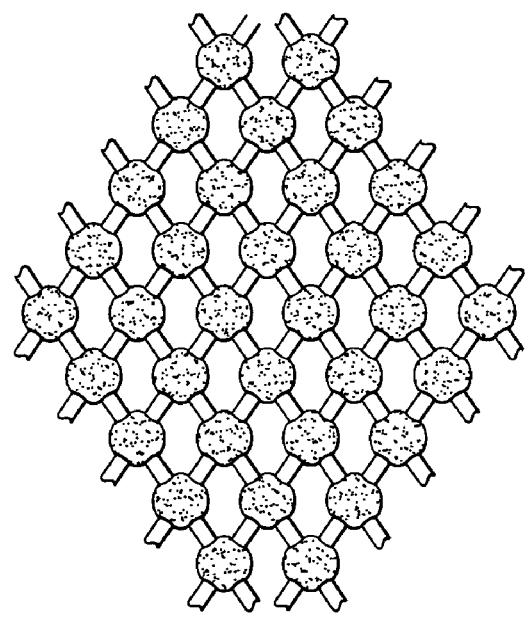
FIG. 5A is an enlarged detail of FIG. 5.

Additionally, knitted prostheses, as shown in FIGS. 4 and 4A, may be used. Knitting involves the interlooping of one yarn system into vertical columns and horizontal rows of loops called wales and courses, respectively, with fabric coming out of the machine in the wales direction. A filament wound prosthesis, as shown in FIGS. 5 and 5A, may also be used where a yarn is transferred from one package to a mandrel to form a prosthesis that is wrapped with the yarn in both directions to provide a biaxial reinforcement. Additionally, a filament spun prosthesis is contemplated wherein yarns are randomly spun onto a mandrel to form a prosthesis.

Advantages of using naphthalene dicarboxylate derivative yarns include the fact that they can withstand powerful methods of sterilization, such as steam sterilization, without affecting their long term properties. Steam sterilization has certain advantages over other types of sterilization in that they may be used in emergency cases when quick implantation of the prothesis is necessary or more sophisticated methods are not available. Additionally, steam sterilizers are highly effective at sterilizing medical items that are able to withstand the high temperature, high moisture and high pressure within the steam sterilization chamber. Steam sterilization employs steam under pressure by using an autoclave. Autoclaves are, in essence, pressure cookers that allow water to be heated to higher temperatures. Since higher pressures allow higher operational temperatures, the sterilization time is desirably reduced. Higher temperatures ensure the efficiency of the sterilization process. Desirably, items used in conjunction with steam sterilization are able to withstand temperatures of at least 100° C. and desirably at least 121° C. and more desirably at least 140° C. Naphthalene dicarboxylate derivative yarns are able retain its properties at extremely high temperatures, for example to about 150° C. As shown in Table 1 and 2, PEN yarns are superior to PET yarns at retaining their physical properties at higher temperatures.

Thus, this invention contemplates a method for making a radiation and thermal resistant and hydrolytically stable steam sterilizable biocompatible prosthesis including the steps of providing a textile fabric having an inner and outer surface and first and second ends and including a plurality of polymeric filaments which include a naphthalene dicarboxylate derivative. Additional steps of this method include selecting a textile construction and forming a prosthesis in accordance with the selected textile pattern. Tubular fabric constructions formed from seamless tubular flat weaving, knitting and braiding are preferred.

The prosthesis of this invention may be sterilized by the end user or, alternatively, by the manufacturer of the material and shipped to the user. Accordingly, this invention further includes a steam sterilized implantable prosthesis that is packaged ready for use. This prosthesis is formed by a process that includes the steps of forming a prosthesis by the method mentioned previously and then steam sterilizing it and maintaining the prosthesis in a sterilized environment until it is ready to be used.

The prostheses of the present invention may be coated with a bio-absorbable coating, such as collagen, albumin, elastin and the like. Such coatings are known in the art and are desirable in vascular and endovascular graft applications to seal the graft and thereby prevent blood loss in the early stages of implantation.

Other coatings which may be used include those disclosed in U.S. Pat. No. 5,851,229, which is incorporated herein. The '229 patent discloses a sealant composition that includes at least two polysaccharides in combination to form a hydrogel or solgel. Sealant compositions may include a bioactive agent and or be cross-linked subsequent to the application of these compositions to the substrate surface. Additionally, U.S. Pat. No. 5,209,776 discloses a composition that includes a first protein component that is preferably collagen and a second protein-supporting component that can be a proteoglycan, a saccharide or a polyalcohol.

The following examples are provided to further illustrate methods of preparation of the inventive prostheses. For all examples, the prosthesis may be of a straight, bifurcated or otherwise designed configuration.

EXAMPLE 1

Woven Construction

A prosthesis is flat woven on an electric jacquard loom in a tubular configuration. A 1/1 plain, tubular weave is used with a warp yarn of textured 50 denier, 48 filament polyethylene naphthalate fully oriented drawn yarn. A flat 115 denier 100 filament partially oriented partially drawn polyethylene naphthalate fill yarns is used with 160 warp ends per inch per layer and 120 pick yarns per inch per layer.

After weaving the prosthesis, the fabric is scoured in a basic solution of warm water, (e.g., 120° F.) and detergent, followed by rinsing to remove the detergent. The prothesis is then attached to a stent fixation device and assembled into a catheter delivery system, or alternatively surgically implanted.

The above is performed with polybutylene naphthalate yarns with excellent results.

EXAMPLE 2

Woven Construction

A graft-stent composite, in accordance with the present invention, is formed from a plain weave tubular fabric having a warp yarn of 50 denier, 48 filament flat polyethylene naphthalate and weft yarn of 50 denier, 48 filament flat polyethylene naphthalate. The ends per square inch are 188 per layer while the picks per inch are 88 per layer. The fabric so formed has a wall thickness of approximately 0.12 mm or less. After weaving into a tubular prosthesis, the prosthesis is scoured to remove dirt, oil and other processing agents. The material is then heat set to stabilize the prosthesis. Heat setting is accomplished by using a conventional oven. The tubular fabric is heat set on smooth mandrels to precisely set the diameter and to remove any creases or wrinkles. The prosthesis is then optionally crimped to impart longitudinal compliance and radial support.

A stent is inserted into the graft (endoprosthesis) to form a stent/graft composite. To secure the stent, it is sutured into place or inserted into a cuff of the graft. Either two stents are inserted at each end of the graft or one stent is inserted at one end. Alternatively, one stent or a series of connected stents may be inserted throughout the length of the graft. Alternatively the stent may be sandwiched between two grafts.

Grafts of the present invention allow for a fabric wall thickness which is thinner than grafts using other materials such as PET due to the durability of the polymer. Additionally, a finer crimp pattern may be imparted to the prosthesis of the present invention as compared to conventional PET grafts. Crimp patterns shown in FIG. 6 includes a series of wave-like crimps therealong. Crimps may be imparted on a finer pitch as the relatively thin fabric would not impede such fine pitch crimping.

EXAMPLE 3

Braided Construction

A regular twill braid is used to produce a tubular prosthesis. The warp yarns and fill yarns are constructed of a two-ply, flat 115 denier, 100 filament partially oriented and partially drawn polyethylene naphthalate yarns. A prosthesis with a diameter of 10 millimeters is achieved using 96 carriers and a 55 degree helix angle.

After braiding the prosthesis, the fabric is scoured in a basic solution of warm water (e.g., 120° F.) and detergent, followed by rinsing to remove the detergent. The prosthesis is then attached to a stent device and assembled into a catheter delivery system for minimally invasive deployment in the body or, alternatively surgically implanted.

EXAMPLE 4

Interlocked 3-D Braided Construction

A tubular prosthesis is formed from an interlocked three-dimensional, multi-layered braided structure, as shown in FIG. 7. The prosthesis is preferably braided on a mandrel at a braid angle of 54.5 degrees. The prosthesis includes four interlocked layers made from a variety of yarns. The first or inner (intraluminal) layer is formed from polyethylene naphthalate polyester yarns, 50 denier, flat 48 filaments having 48 ends (ends refer to the number of carriers within the braiding machine). The second layer is formed having a fusible component. More specifically, this layer includes a 40 cotton count (spun) Cell Bond™ fusible yarn having 12 ends and a 50 denier, flat, polyethylene naphthalate (PEN) polyester yarn having 48 ends. Cell Bond™ is a biocomponent yarn which has a core and sheath, whereby the sheath has a different melting temperature than the core. The third layer is formed from a 3 mm diameter polyethylene naphthalate monofilament yarn having 48 ends. This yarn provides the braided prosthesis with a stiffening component. The fourth (outer) layer is formed of polyethylene naphthalate polyester 50 denier, textured, 48 filament yarn with 48 ends. Upon completion, the braided structure is cleaned or scoured and subsequently heat conditioned in a convection oven at about 175° C. for about 20 minutes to melt the fusible component and heat set the polyethylene naphthalate polyester yarns.

EXAMPLE 5

Solid 3-D Braided Construction

A tubular prosthesis is formed from a solid three-dimensional braided structure, as shown in FIG. 8, having six strands forming three plies which are interbraided through the thickness of the braid. The prosthesis is formed from 50 denier, 48 filament, textured polyethylene naphthalate polyester yarn on each carrier in the machine, for a total of 144 ends (48 ends per pair or set of yarns). Upon completion of the braid, the structure is cleaned and subsequently heat-conditioned in a convection oven at a temperature of about 175° C. for about 20 minutes to heat set the polyethylene naphthalate polyester yarns.

EXAMPLE 6

Weft Knitted Construction

A tubular jersey weft knit is used with a three-ply, flat 115 denier, 100 filament partially oriented and partially drawn polyethylene naphthalate yarns with 30 wales per inch per layer and 40 courses per inch per layer. After knitting, the fabric is scoured in a basic solution of warm water (e.g., 120° F.) and detergent. It is rinsed to remove the cleaning agents.

The prosthesis is then attached to a stent device and assembled into a catheter delivery system for insertion into the body or alternatively directly implanted. The knitted fabric geometry provides an additional amount of stretch of about 50% to the overall dilation of the prosthesis. A warp knit construction can also be used. For example, instead of a tubular jersey weft knit construction, a tubular double tri-cotton warp knit construction with similar stitched density to the tubular jersey weft knit can be used.

EXAMPLE 7

Filament Wound Construction

A one-ply, flat 115 denier, 110 filament partially oriented polyethylene naphthalate yarn is filament wound onto a mandrel of known diameter. The helix angle achieved is about 55 degrees. The mandrel is wrapped with the yarn in both directions to provide biaxial reinforcement. To hold the yarns in place, they are passed through a solution of solvated polyurethane elastomer, such a BIOMARK® solution, sold by Johnson & Johnson. The solvent is removed, causing the polyurethane to dry and glue the yarns together.

After filament winding, the material is scoured in a basic solution of warn water (e.g., 120° F.) and detergent, followed by rinsing to remove the detergent. The prothesis can then be attached to a stent fixation device and assembled into a catheter delivery system for delivery intraluminally or directly implanted.

Additionally, each of the above prostheses are steam sterilized in an autoclave. The autoclave consists of an empty chamber made from stainless steel using a method for adding water under pressure to the chamber, heating coils, and a pressure relief valve so that a given pressure is maintained.

EXAMPLE 8

The spinning conditions are shown in Table 3. Spinning conditions were set to produce a yarn with a linear density of 30–70 d, a tenacity of about 9 g/den. The PEN yarn is subsequently dried carefully. Typical extrusion conditions are set forth in Table 4. Seven spools of PEN yarn were analyzed for denier and tensile properties using an analytical balance and Instron 5500. Results of the analysis are shown in Table 5.

TABLE I

Properties of PEN and PET Monofilament

|  | PEN* |  | PET |
| --- | --- | --- | --- |
| Carboxyl end group content μ-equivalents/g | 39 | 30 | 9 |
| Tensile strength, g/d | 5.65 | 5.2 | 5.46 |
| Elongation, % | 26.2 | 19.2 | 23.8 |
| Tensile, strength retention, % 150° C., 6 hrs water | 75 | 25 | 45 |
| 150° C., 5 days 5% $H_2SO_4$ | 70 | 5 | 10 |
| 100° C., 4 hrs 20% caustic | 40 | 0 | 5 |
| Resistance to moist heat, days 120° C. in $H_2O$ to reduce tenacity to <1 g. d | 40 | 5 | 10 |

*The PEN monofilament was produced from a 0.64 IV polymer.
Spinning was conducted at 305° C. at 900 m/min.
The undrawn yarn was spun at 155° C. at a draw ratio of 3.3 followed by heat treatment at 250° C..

TABLE 2

Properties of PEN vs. Other Industrial Fibers

|  | PEN | PET | NYLON 6/6 |
| --- | --- | --- | --- |
| Tenacity (g/denier) | 8.5–10.9 | 6–9 | 6–9 |
| Modulus (g/denier) | 200–250 | 45–78 | 21–58 |
| % Shrinkage, boiling water | 1–2 | 1.5–5 | 5–10 |
| Glass Transition | 121° C. | 78° C. | — |
| Thermal Resistance | 160° C. | 120° C. | — |

TABLE 3

Spinning Conditions

| Spinning Temperature | 305–315° C. |
| --- | --- |
| Spinnerette Holes Diameter | .5 mm with L/D = <2 |
| Drying Conditions | 150–170° C. for 16–24 hrs. |
| Extrusion Temp.: | 300–320° C. |
| Heating Chamber Below The Spinnerette | Held at 300–350° C. and 30 to 50 cm long |
| Take Up Speed | 500 to 1000 m/min |

TABLE 4

Resin Properties

| | |
|---|---|
| Melting Temp.: | 268–275° C. |
| Tg: | 121° C. |
| Intrinsic Viscosity: | ICI X-11: 0.831 |
| | ICI X-60: 1.705 |
| | Shell Vituf 40027: 0.50 |
| | Shell Vituf SLX7: 0.70 |

TABLE 5

Analysis of Spun PEN Yarns*

| Sample | | Denier (g/len) | | Strength (g) | | Elongation (%) | | Tenacity (g/den) | | I. Mod (g.den) | | Draw Ratio & Temp | | Notes (Spinning Conditions) |
|---|---|---|---|---|---|---|---|---|---|---|---|---|---|---|
| 1 PEN | Avg. | 1700.4 | Avg. | 1053.0 | Avg. | 3.22 | Avg. | .619 | Avg. | 21.22 | D.R. | 1.07 | | As spun, no drawing or heat. |
| | Std. | 131.99 | Std. | 102 | Std. | .094 | Std. | .060 | Std. | .886 | Temp. | 60° C. | | |
| | C.V. | 7.76% | C.V. | 9.7% | C.V. | 2.9% | C.V. | 9.7% | C.V. | 4.2% | | | | |
| 3 PEN | Avg. | 1765.8 | Avg. | 1217 | Avg. | 4.17 | Avg. | .689 | Avg. | 20.3 | D.R. | 1.14 | | As spun, face heater set @ |
| | Std. | 40.42 | Std. | 39.6 | Std. | .002 | Std. | .022 | Std. | .719 | Temp. | 60° C. | | 305° C. |
| | C.V. | 2.29% | C.V. | 3.2% | C.V. | .046% | C.V. | 3.2% | C.V. | 3.5% | | | | |
| 3B PEN | Avg. | 1785.6 | Avg. | 1164 | Avg. | 4.06 | Avg. | .652 | Avg. | 19.29 | D.R. | 1.14 | | As spun, face heater set @ |
| | Std. | 36.4 | Std. | 126.5 | Std. | .099 | Std. | .071 | Std. | .906 | Temp. | 60° C. | | 305° C. |
| | C.V. | 2.04% | C.V. | 10.8% | C.V. | 2.44% | C.V. | 10.9% | C.V. | 4.7% | | | | |
| 4 PEN | Avg. | 1767.6 | Avg. | 1113 | Avg. | 4.060 | Avg. | .630 | Avg. | 19.62 | D.R. | 1.14 | | Some quench air. |
| | Std. | 54.48 | Std. | 76.6 | Std. | .098 | Std. | .045 | Std. | 1.315 | Temp. | 60° C. | | |
| | C.V. | 3.08% | C.V. | 7.15% | C.V. | 2.41% | C.V. | 7.15% | C.V. | 6.7% | | | | |
| 6 PEN | Avg. | 277.5 | Avg. | 1338 | Avg. | 11.78 | Avg. | 4.823 | Avg. | 107.13 | D.R. | 2.86 | | No quench some drawing |
| | Std. | 20.05 | Std. | 39.98 | Std. | 1.182 | Std. | .144 | Std. | 3.145 | Temp. | 90° C. | | |
| | C.V. | 7.23% | C.V. | 2.98% | C.V. | 10.03% | C.V. | 2.98% | C.V. | 2.9% | | | | |
| 7 PEN | Avg. | 330.0 | Avg. | 1688 | Avg. | 12.22 | Avg. | 5.11 | Avg. | 127.8 | D.R. | 5.6 | | |
| | Std. | 5.27 | Std. | 59.9 | Std. | 1.29 | Std. | .181 | Std. | 6.79 | Temp. | 90° C. | | |
| | C.V. | 1.6% | C.V. | 3.5% | C.V. | 10.6% | C.V. | 3.54% | C.V. | 5.3% | | | | |
| 8 PEN | Avg. | 316.2 | Avg. | 1630 | Avg. | 7.84 | Avg. | 5.156 | Avg. | 111.6 | D.R. | 7.7 | | Melt temp 315° C. |
| | Std. | 8.17 | Std. | 7.58 | Std. | .498 | Std. | .024 | Std. | 10.07 | Temp. | 105° C. | | |
| | C.V. | 2.58% | C.V. | .465% | C.V. | 6.35% | C.V. | .465% | C.V. | 9.0% | | | | |

*Yarns produced with extruder setting of 266° C., 270° C., 305° C., 325° C. (head); 4 × 32 holes spinnerette; L/D = 2.

The invention being thus described it will now be evident to those skilled in the art that the same may be varied in many ways. Such variations are not to be regarded as a departure from the spirit and scope of the invention and all such modifications are intended to be included within the scope of the following claims.

What is claimed is:

1. An implantable prosthesis having improved mechanical and chemical properties comprising:
   a radiation resistant and hydrolytically stable biocompatible fabric having inner and outer surfaces and first and second ends;
   said fabric having a woven textile construction comprising a plurality of radial filaments and a plurality of longitudinal filaments, said longitudinal filaments being disposed longitudinally along the length of said prosthesis and said radial filaments being disposed generally perpendicularly to said longitudinal filaments, said longitudinal filaments and said radial filaments comprising at least two naphthalene dicarboxylate derivatives, wherein said radiation resistant and hydrolytically stable biocompatible fabric is stable at a temperature of at least about 120° C.,
   and wherein said radial filaments comprises a combination of undrawn and partially drawn radial filaments.

2. The implantable prosthesis of claim 1 wherein said fabric is polyethylene naphthalate.

3. The implantable prosthesis of claim 1 wherein said fabric is selected from the group consisting of poly(ethylene napthalate), poly(propylene naphthalate), polytrimethylene naphthalate, trimethylenediol naphthalate, poly(iso-propylene naphthalate), poly(n-butylene naphthalate), poly(isobutylene naphthalate), poly(tert-butylene naphthalate), poly(n-pentylene naphthatate), poly(n-hexylene naphthalate), and combinations and derivatives thereof.

4. The implantable prosthesis according to claim 1 wherein said implantable prosthesis is a vascular graft.

5. The implantable prosthesis according to claim 1 wherein said implantable prosthesis is an endovascular graft.

6. The implantable prosthesis according to claim 1 further including a coating.

7. The implantable prosthesis according to claim 1, wherein the polymeric filaments have about 20 to about 100 filaments.

8. The implantable prosthesis according to claim 1, wherein the polymeric filaments have a denier from about 20 to about 1500.

9. The implantable prosthesis according to claim 1, wherein said partially drawn and undrawn polymeric filaments are capable of circumferential expansion.

10. An implantable prosthesis having improved mechanical and chemical properties comprising:
    a radiation resistant and hydrolytically stable biocompatible tubular fabric of a textile construction,
    said fabric having a plurality of yarns comprising polyethylene naphthalate and polybutylene naphthalate, wherein said radiation resistant and hydrolytically stable biocompatible fabric is stable at a temperature of at least about 120° C.,
    and wherein said plurality of polymeric filaments comprises a combination of undrawn and partially drawn radial filaments.

11. The implantable prosthesis according to claim 10 wherein said implantable prosthesis is a intraluminal prosthesis.

12. The implantable prosthesis according to claim 10 wherein said implantable prosthesis is an endovascular graft.

13. The implantable prosthesis according to claim 10 further including a radially deformable support component.

14. The implantable prosthesis according to claim 13 wherein said support component is a radially deformable stent.

15. Method for making a radiation and thermal resistant and hydrolytically stable, steam sterilizable biocompatible prosthesis comprising:
   a) partially drawing a plurality of polymeric filaments comprising at least two naphthalene dicarboxylate derivatives;
   b) forming a fabric having an inner and outer surface and first and second ends, said fabric having a woven textile construction comprising a plurality of radial filaments and a plurality of longitudinal filaments, said longitudinal filaments being disposed longitudinally along the length of said prosthesis and said radial filaments being disposed generally perpendicularly to said longitudinal filaments, said radial filaments comprising a combination of said partially drawn polymeric filaments and undrawn polymeric filaments, wherein said fabric being stable at a temperature of at least about 120° C.; and
   c) forming said prosthesis from said fabric.

16. An implantable prosthesis having improved mechanical and chemical properties comprising:
   a radiation resistant and hydrolytically stable biocompatible fabric having inner and outer surfaces and first and second ends;
   said fabric having a textile construction of a plurality of polymeric filaments which comprises a combination of undrawn and partially drawn radial filaments comprising at least two naphthalene dicarboxylate derivatives, wherein said radiation resistant and hydrolytically stable biocompatible fabric is stable at a temperature of at least about 120° C.,
   wherein said naphthalene dicarboxylate derivatives conforms to the formula:

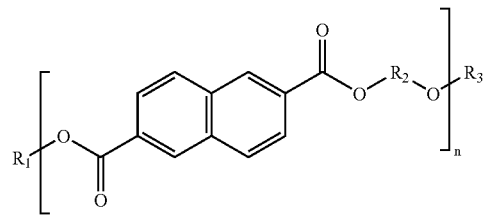

wherein $R_1$ and $R_3$ are the same or different groups and are independently selected from the group consisting of hydrogen radicals and methyl radicals; $R_2$ is an alkylene radical having 1 to 6 carbon atoms which may be linear or branched; and n is from about 10 to about 200, and wherein said prosthesis further comprises a series of crimps.

17. An implantable prosthesis having improved mechanical and chemical properties comprising:
   a radiation resistant and hydrolytically stable biocompatible fabric having inner and outer surfaces and first and second ends;
   said fabric having a woven textile construction comprising a plurality of radial filaments and a plurality of longitudinal filaments, said longitudinal filaments being disposed longitudinally along the length of said prosthesis and said radial filaments being disposed generally perpendicularly to said longitudinal filaments, said longitudinal filaments and said radial filaments comprising a naphthalene dicarboxylate derivative, wherein said radiation resistant and hydrolytically stable biocompatible fabric is stable at a temperature of at least about 120° C.,
   and wherein said radial filaments comprises a combination of undrawn and partially drawn radial filaments.

* * * * *